United States Patent
Roy et al.

(10) Patent No.: US 9,434,749 B2
(45) Date of Patent: Sep. 6, 2016

(54) PLATINUM CATALYZED HYDROSILYLATION REACTIONS UTILIZING CYCLODIENE ADDITIVES

(71) Applicant: Momentive Performance Materials Inc., Waterford, NY (US)

(72) Inventors: Aroop Kumar Roy, Mechanicville, NY (US); Julie L. Boyer, Watervliet, NY (US); Juergen Koller, Vienna, WV (US); David Jenkins, Cohoes, NY (US); Andrea Trotto, Termoli (IT); Kenrick M. Lewis, Flushing, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/737,930

(22) Filed: Jun. 12, 2015

(65) Prior Publication Data
US 2015/0361112 A1 Dec. 17, 2015

Related U.S. Application Data

(60) Provisional application No. 62/011,825, filed on Jun. 13, 2014.

(51) Int. Cl.
| | | |
|---|---|---|
| C07F 7/04 | (2006.01) | |
| C07F 7/08 | (2006.01) | |
| C07F 7/12 | (2006.01) | |
| C07F 7/14 | (2006.01) | |
| C07F 7/18 | (2006.01) | |

(52) U.S. Cl.
CPC ............ *C07F 7/0829* (2013.01); *C07F 7/0879* (2013.01); *C07F 7/12* (2013.01); *C07F 7/14* (2013.01); *C07F 7/1836* (2013.01)

(58) Field of Classification Search
CPC ....... C07F 7/0829; C07F 7/14; C07F 7/1836
USPC ......................................................... 556/438
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,775,452 A | 11/1973 | Karstedt | |
| 5,563,287 A * | 10/1996 | Roy | C07F 7/14 556/479 |
| 5,567,848 A | 10/1996 | Roy | |
| 6,605,734 B2 | 8/2003 | Roy et al. | |

FOREIGN PATENT DOCUMENTS

| | | |
|---|---|---|
| EP | 0785202 | 7/1997 |
| JP | 54076529 A | 6/1979 |
| JP | 54076530 A | 6/1979 |
| WO | 03050130 | 6/2003 |

OTHER PUBLICATIONS

Roy, et al., "The First Alkene-Platinum-Silyl Complexes: Lifting the Hydrosilation Mechanism Shroud with Long-Lived Precatalytic Intermediates and True Pt Catalysts." J. Am. Chem. Soc. 2002, 124, 9510-9524.
Speier, et al., "The Addition of Silicon Hydrides to Olefinic Double Bonds. Part II. The Use of Group VIII Metal Catalysts" J. Am. Chem. Soc. 79, 974 (1957).
Lewis et al., "Platinum-Catalyzed Hydrosilylation of Alkynes" Organometallics, 1991, 10, 3750-3759.
Caseri et al., "Hydrosilylation Chemistry and Catalysis with cis-PcLC2(PhCH+CH2)2" Organometallics, 1988, 7, 1373-1380.
PCT International Search Report and Written Opinion for PCT/US2015/035594, mailed Sep. 16, 2015, International Search Authority/European Patent Office, Netherlands.
Downing, et al., "Diethyl Sulfide Stabilization of Platinum-Complex Catalysts for Hydrosilylation of Olefins." Catalysis Communications, Mar. 30, 2011, vol. 12, No. 12, pp. 1166-1169, Elsevier Science, Amsterdam, NL.
Sprenger, et al., "Stable Platinum(0) Catalysts for Catalytic Hydrosilylation of Styrene and Synthesis of [Pt (Ar-bian)([eta]2-alkene)] Complexes." European Journal of Inorganic Chemistry, Oct. 1, 2003, vol. 2003, No. 20, pp. 3811-3819.

* cited by examiner

*Primary Examiner* — Porfirio Nazario Gonzalez
*Assistant Examiner* — Kofi Adzamli
(74) *Attorney, Agent, or Firm* — Joseph E. Waters; McDonald Hopkins LLC

(57) ABSTRACT

A process for the hydrosilylation of an unsaturated compound comprising reacting (a) a silyl hydride with (b) an unsaturated compound in the presence of (c) a platinum compound and (d) a cyclodiene, with the provisos that (i) when the unsaturated compound is a terminal alkyne, the silyl hydride is other than a halosilane, and (ii) when the platinum compound is a Pt(II)-based compound, the ratio of total moles of cyclodiene to moles of platinum is less than 3:1.

23 Claims, 3 Drawing Sheets

PLATINUM CATALYZED HYDROSILYLATION REACTIONS UTILIZING CYCLODIENE ADDITIVES

CROSS REFERENCE TO RELATED APPLICATIONS

The present application claims priority to and the benefit of U.S. Provisional Application No. 62/011,825 titled "Platinum Catalyzed Hydrosilylation Reactions Utilizing Cyclodiene Additives" filed on Jun. 13, 2014, the disclosure of which is incorporated herein by reference in its entirety.

FIELD OF THE INVENTION

The present invention relates generally to the use of cyclodiene additives for improved catalyst performance in platinum catalyzed hydrosilylation reactions.

BACKGROUND

Hydrosilylation chemistry, involving the reaction between a silylhydride and an unsaturated organic group, is the basis for synthetic routes to produce commercial silicone products such as silicone surfactants, silicone fluids and organosilanes. Conventionally, hydrosilylation reactions have been catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal compounds and complexes are widely employed commercially as catalysts for hydrosilylation reactions, they have several distinct disadvantages. One disadvantage of the current catalyst systems is the undesired color imparted to the final product. This yellow coloration or Pt precipitation in crude products often necessitates additional and costly purification steps. Another distinct disadvantage of the current systems is the progressive deactivation of the platinum catalysts during the course of the reaction which necessitates higher loadings of this costly metal. Yet another disadvantage encountered with Pt-catalyzed hydrosilylation of unsaturated and COH-terminated oligo- or polyethers is the undesired reaction of SiH with the alcohol OH, which produces SiOC linkages that waste SiH groups, leave unreacted C=C bonds, and can cause performance problems.

Due to the high price of precious metals, catalysts derived from these platinum metals can constitute a significant proportion of the cost of organosilane and silicone products. Over the last two decades, global demand for precious metals, including platinum, has sharply increased, driving prices several hundred folds higher, thereby precipitating the need for effective, yet lower catalyst loadings. There is a need in the silicone industry for platinum catalysts of improved stability. This improved stability would enable the lowering of Pt catalyst loadings and decreasing cycle time in reactors and improving yield for many hydrosilylations.

The use of pre-formed Pt-COD complexes (COD=1,5-cyclooctadiene) in hydrosilylation reactions has been previously reported, e.g., JP 54076530A, JP 54076529A, L. Lewis et al., Organometallics, 1991, 10, 3750-3759, and P. Pregosin et al., Organometallics, 1988, 7, 1373-1380. $PtCODCl_2$, $PtCODMe_2$, and $PtCODPh_2$ are commercially available and their use as catalysts for hydrosilylation has been known for many years. Roy et al. have reported the preparation of a series of $PtCOD(SiR_3)_2$ compounds from $PtCODCl_2$ (Roy, Aroop K.; Taylor, Richard B. J. Am Chem. Soc., 2012, 124, 9510-9524; and U.S. Pat. No. 6,605,734). Notably, the preparation of these $CODPtSi_2$ complexes strictly requires the use of at least three equivalents of COD per equivalent of Pt, even when prepared in situ for hydrosilylation catalysis, as COD is lost to both hydrogenation and isomerization (1,4-COD and 1,3-COD) reactions. This critical stoichiometry of COD/Pt is delineated both in the above patent and the JACS publication. Further, the use of only one COD per Pt led to no identifiable COD-Pt species, as reported in the JACS publication.

The use of COD as an additive has been shown to reduce the amount of bis-silylated product in hydrosilylation of only alkynes with hydrochlorosilanes in U.S. Pat. No. 5,563,287. Other cyclodiene complexes of platinum are also known and commercially available, such as (norbornadiene) $PtCl_2$ and (dicyclopentadiene) $PtCl_2$ but again, these latter diene complexes are not known to provide any particular benefit over catalysts such as Speier's or Karstedt's.

SUMMARY

The present invention describes the use of cyclodiene additives to stabilize the platinum catalysts in hydrosilylation reactions. It has been found that cyclodiene additives are suitable for use in hydrosilylation reactions with a variety of unsaturated compounds and silanes. The stabilization can be achieved using a relatively low amount of cyclodiene additive. The use of cyclodiene additives may also allow for decreasing the platinum loading in hydrosilylation reactions. It has now been surprisingly found that cyclodiene additives, such as cyclooctadienes, can be used to stabilize platinum catalyst in hydrosilylation reactions. The stabilization can be observed, for example, by the ability to use lower platinum loadings in hydrosilylation reactions, improved color of the hydrosilylation products, and/or reduction of side reactions occurring during the process. The cyclodiene additives used may include 1,5-cyclooctadiene.

The present inventors have now unexpectedly discovered that the use of cyclodienes such as COD as additives, even at cyclodiene:Pt ratio as low as 1:1 and 2:1, and in conjunction with common Pt catalysts such as Speier's or Karstedt's helps stabilize active platinum catalysts in hydrosilylation reactions and leads to highly desirable catalysis improvements such as reduced level of Pt use, color reduction, reduction in by-products and shorter reaction time.

In one aspect, the present invention provides a process for the hydrosilylation of an unsaturated compound comprising reacting (a) a silyl hydride with (b) an unsaturated compound in the presence of (c) a platinum compound and (d) a cyclodiene, with the provisos that (i) when the unsaturated compound is a terminal alkyne, the silyl hydride is other than a halosilane, and (ii) when the platinum compound is a Pt(II)-based compound, the ratio of total moles of cyclodiene to moles of platinum is less than 3:1.

In an embodiment, the cyclodiene is chosen from a compound of the formula:

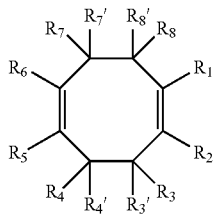

wherein $R^1$-$R^8$, $R^{3'}$, $R^{4'}$, $R^{7'}$, and $R^{8'}$ are independently hydrogen; an substituted or unsubstituted alkyl or aryl group optionally containing at least one heteroatom; an alkoxy; and a halogen radical; optionally $R^1$-$R^2$ and/or $R^5$-$R^6$ taken together may form a ring structure.

In one embodiment, the cyclodiene comprises 1,5-cyclooctadiene; 1,5-dimethyl-1,5-cyclooctadiene; 1,6-dimethyl-1,5-cyclooctadiene, or a combination of two or more thereof.

The present technology also provides a process according to any of the previous embodiments, where the platinum compound is a Pt(II)-based compound, and the ratio of total moles of cyclodiene additive to moles of platinum is less than 2:1.

The present technology also provides a process according to any of the previous embodiments, where the platinum compound is a Pt(II)-based compound, and the ratio of total moles of cyclodiene additive to moles of platinum is about 1:1 or lower.

The present technology also provides a process according to any of the previous embodiments, where the platinum compound is a Pt(II)-based compound, and the ratio of total moles of cyclodiene additive to moles of platinum is from about 0.1:1 to about 2:1.

The present technology also provides a process according to any of the previous embodiments, where the platinum compound is a Pt(0)-based compound.

The present technology also provides a process according to any of the previous embodiments, where the platinum compound is chosen from a vinylsiloxane-complexed Pt catalyst.

The present technology also provides a process according to any of the previous embodiments, where the ratio of cyclodiene to Pt(0) is 0.1:1 to 100:1

The present technology also provides a process according to any of the previous embodiments, where the unsaturated compound is chosen from an unsaturated polyether; an alkyl capped allyl polyether; a methylallyl polyether; a terminally unsaturated amine; an alkyne; a C2-C45 linear or branched olefin; an unsaturated epoxide; a terminally unsaturated acrylate; a terminally unsaturated methacrylate; a terminally unsaturated diene; an aliphatically unsaturated aryl ether; an aliphatically unsaturated aromatic hydrocarbon; an unsaturated cycloalkane; a vinyl-functionalized polymer or oligomer; a vinyl-functionalized and/or terminally unsaturated allyl-functionalized or alkenyl-functionalized silane or siloxane; an unsaturated fatty acid; an unsaturated fatty ester; an aliphatically unsaturated synthetic or natural mineral; or a combination of two or more thereof.

The present technology also provides a process according to any of the previous embodiments, where the unsaturated compound is chosen from polyoxyalkylenes having the general formula:

$$R^{25}(OCH_2CH_2)_z(OCH_2CHR^{27})_w\!-\!OR^{26};$$

$$R^{26}O(CHR^{27}CH_2O)_w(CH_2CH_2O)_z\!-\!CR^{28}_2\!-\!C\!\equiv\!C\!-\!CR^{28}_2(OCH_2CH_2)_z(OCH_2CHR^{27})_wOR^{26}$$

$$H_2C\!=\!CR^{28}CH_2O(CH_2CH_2O)_z(CH_2CHR^{27}O)_wCH_2CR^{28}\!=\!CH_2$$

wherein $R^{25}$ is independently an unsaturated organic group containing from 2 to 10 carbon atoms; $R^{26}$ is independently hydrogen, an acyl group, or an alkyl group having from 1 to 8 carbon atoms; $R^{27}$ is independently a monovalent hydrocarbon group; $R^{28}$ independently chosen from hydrogen and a monovalent hydrocarbon group; each occurrence of z is 0 to 100 inclusive; and each occurrence of w is 0 to 100 inclusive.

The present technology also provides a process according to any of the previous embodiments, where the silylhydride is chosen from a compound of the formula $R^9{}_m SiH_p X_{4-(m+p)}$ and/or $M_a M^H{}_b D_c D^H{}_d T_e T^H{}_f Q_g$, where each $R^9$ is independently a substituted or unsubstituted aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M represents a monofunctional group of formula $R^{10}{}_3 SiO_{1/2}$, a D represents a difunctional group of formula $R^{11}{}_2 SiO_{2/2}$, a T represents a trifunctional group of formula $R^{12} SiO_{3/2}$, Q represents a tetrafunctional group of formula $SiO_{4/2}$, $M^H$ represents $HR^{13}{}_2 SiO_{1/2}$, $T^H$ represents $HSiO_{3/2}$, and $D^H$ represents $R^{14} HSiO_{2/2}$; each occurrence of $R^{10-14}$ is independently C1-C18 alkyl, C1-C18 substituted alkyl, C6-C14 aryl or substituted aryl, wherein R10-14 optionally contains at least one heteroatom.

The present technology also provides a process according to any of the previous embodiments, where the silylhydride is a chlorosilane.

The present technology also provides a process according to any of the previous embodiments, where the silylhydride is a compound of the formula $R^{15}R^{16}R^{17}Si(CH_2R^{18})_x SiOSiR^{19}R^{20}(OSiR^{21}R^{22})_y OSiR^{23}R^{24}H$, where $R^{15}$-$R^{24}$ are independently chosen from hydrogen, a monovalent alkyl group, a cycloalkyl group, and an aryl group; x has a value of 1-8, and y has a value from zero to 10.

The present technology also provides a process according to any of the previous embodiments, where the ratio of cyclodiene to platinum is about 1:1.

The present technology also provides a process according to any of the previous embodiments, where the platinum compound is chosen from platinum halides, platinum siloxane complexes, cycloalkadiene-platinum complexes, or a combination of two or more thereof.

The present technology also provides a process according to any of the previous embodiments, where the platinum compound is chloroplatinic acid.

The present technology also provides a process according to any of the previous embodiments, where the unsaturated compound is allyl methacrylate.

The present technology also provides a process according to any of the previous embodiments, where the unsaturated compound is allyl glycidyl ether.

The present technology also provides a process according to any of the previous embodiments, where the unsaturated compound is an allyl or methallyl polyether.

The present technology also provides a process according to any of the previous embodiments, where the reaction is carried out at a temperature of −50° C. to 250° C.

The present technology also provides a process according to any of the previous embodiments, where the reaction is conducted in the presence of a solvent chosen from a hydrocarbon, a halogenated hydrocarbon, an ether, an alcohol, or a combination of two or more thereof.

The present technology also provides a process according to any of the previous embodiments, where the platinum concentration is from about 100 parts per billion to about 100 parts per million.

In another aspect, the present invention provides a silylated product produced from the process according to any of the previous embodiments.

DETAILED DESCRIPTION

Figure 1:
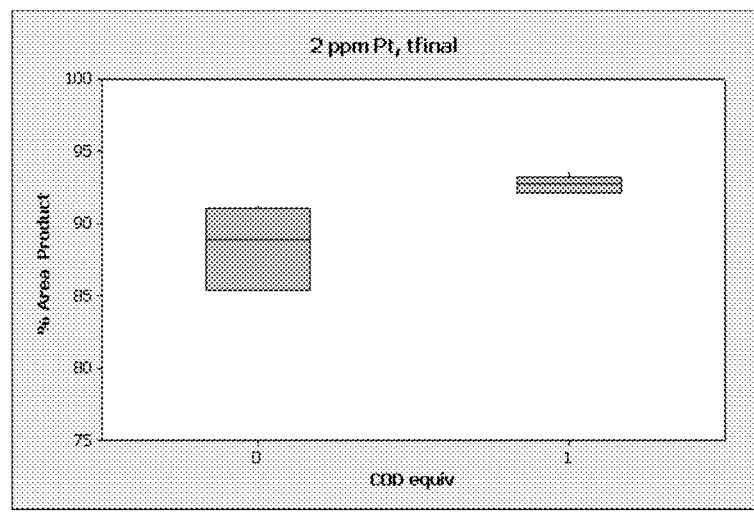
FIG. 1 is a graph showing the product yield for reactions of allyl methacrylate and SiMeCl$_2$H as determined by GC analysis for reactions runs with and without COD additives.

The present invention provides a process for the hydrosilylation of a composition containing a silylhydride and a compound containing at least one unsaturated group in the presence of a platinum catalyst and cyclodiene compound.

As used herein, the term "alkyl" includes straight, branched, and/or cyclic alkyl groups. Specific and non-limiting examples of alkyls include, but are not limited to, methyl, ethyl, propyl, isobutyl, cyclopentyl, cyclohexyl, etc. Still other examples of alkyls include alkyls substituted with a heteroatom, including cyclic groups with a heteroatom in the ring.

As used herein, the term "substituted alkyl" includes an alkyl group that contains one or more substituent groups that are inert under the process conditions to which the compound containing these groups is subjected. The substituent groups also do not substantially or deleteriously interfere with the process. The alkyl and substituted alkyl groups can include one or more heteroatoms. In one embodiment, a substituted alkyl may comprise an alkylsilyl group. Examples of alkylsilyl groups include, but are not limited to alkylsilyl groups having 3-20 carbon atoms such as a trimethylsilyl group, a triethylsilyl group, a triisopropylsilyl group, etc. Optionally, the silyl moiety of the alkylsilyl group may also be represented by phenyldimethylsilyl, diphenylmethylsilyl, or triphenylsilyl.

As used herein, the term "alkoxy" refers to a monovalent group of the formula —OR, where R is an alkyl group. Non-limiting examples of alkoxy groups include, for example, methoxy, ethoxy, propoxy, butoxy, benzyloxy, etc.

As used herein, the term "aryl" refers to a non-limiting group of any aromatic hydrocarbon from which one hydrogen atom has been removed. An aryl may have one or more aromatic rings, which may be fused, connected by single bonds or other groups. Examples of suitable aryls include, but are not limited to, tolyl, xylyl, phenyl, and naphthalenyl.

As used herein, the term "substituted aryl" refers to an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the attachment can be through a heteroatom (such as nitrogen) of the heteroaromatic ring instead of a carbon. In one embodiment, the substituted aryl groups herein contain 6 to about 30 carbon atoms.

As used herein, the term "alkenyl" refers to any straight, branched, or cyclic alkenyl group containing one or more carbon-carbon double bonds, where the point of substitution can be either a carbon-carbon double bond or elsewhere in the group. Examples of suitable alkenyls include, but are not limited to, vinyl, propenyl, allyl, methallyl, ethylidenyl norbornyl, etc.

As used herein, the term "alkynyl" refers to any straight, branched, or cyclic alkynyl group containing one or more carbon-carbon triple bonds, where the point of substitution can be either at a carbon-carbon triple bond or elsewhere in the group.

As used herein, the term "unsaturated" refers to one or more double or triple bonds. In one embodiment, it refers to carbon-carbon double or triple bonds.

As used herein, the term "inert substituent" refers to a group other than hydrocarbyl or substituted hydrocarbyl, which is inert under the process conditions to which the compound containing the group is subjected. The inert substituents also do not substantially or deleteriously interfere with any process described herein that the compound in which they are present may take part in. Examples of inert substituents include, but are not limited to, halo (fluoro, chloro, bromo, and iodo), and ether such as —OR$^{30}$ wherein R$^{30}$ is hydrocarbyl or substituted hydrocarbyl.

As used herein, the term "hetero atoms" refers to any of the Group 13-17 elements except carbon, and can include, for example, oxygen, nitrogen, silicon, sulfur, phosphorus, fluorine, chlorine, bromine, and iodine.

As used herein, the term "olefin" refers to any aliphatic or aromatic hydrocarbon also containing one or more aliphatic carbon-carbon unsaturations. Such olefins may be linear, branched, or cyclic and may be substituted with heteroatoms as described above, with the proviso that the substituents do not interfere substantially or deleteriously with the course of the desired reaction to produce the dehydrogenatively silylated product.

The cyclodiene of this invention is represented by Formula I:

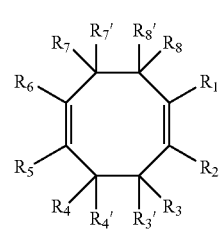

Formula I wherein $R^1$-$R^8$, $R^{3'}$, $R^{4'}$, $R^{7'}$, and $R^{8'}$ are independently a H or substituted or unsubstituted alkyl or aryl group optionally containing at least one heteroatom. $R^1$-$R^8$ may also independently represent a halide or alkoxy group. Furthermore, $R^1$-$R^2$ and $R^5$-$R^6$ taken together, or independently, may form a ring. In embodiments, $R^1$-$R^8$, $R^{3'}$, $R^{4'}$, $R^{7'}$, and $R^{8'}$ are independently chosen from H, a C1-C18 alkyl, a C1-C18 substituted alkyl, a C6-C14 aryl, and a substituted aryl. In embodiments, $R^1$-$R^8$, $R^{3'}$, $R^{4'}$, $R^{7'}$, and $R^{8'}$ are independently chosen from H, a C1-C16 alkyl, a C1-C16 substituted alkyl, a C6-C10 aryl, and a substituted aryl. Examples of suitable compounds of Formula I, include but are not limited to, 1,5-cyclooctadiene, 1,5-dimethyl-1,5-cyclooctadiene, 1,6-dimethyl-1,5-cyclooctadiene, and mixtures of two or more thereof.

The cyclodiene additive may be provided based on the valence state of the platinum in the platinum compound. In embodiments, the platinum compound is a Pt(II) compounds, and the cyclodiene additive is provided such that the molar equivalent ratio of cyclodiene additive to platinum is less than 3:1. In one embodiment, the ratio of cyclodiene to Pt(II) is 2:1, 1.5:1 1:1; 0.5:1; even 0.1:1. In one embodiment, the cyclodiene to platinum (Pt(II)) ratio is from about 0.1:1 to about 2:1; from about 0.25:1 to about 1.5:1; even from about 0.5:1 to about 1:1. It will be appreciated that the ratio of cyclodiene to platinum includes all fractional ratios within the particular ranges. In embodiments when the platinum compound is a Pt(0) compound, the ratio of total moles of cyclodiene additive to moles of platinum may be from about 0.1:1 to about 100:1; from about 0.5:1 to about 50:1; even from about 1:1 to about 5:1. The practical ratio of cyclodiene to platinum (0) is determined by any deleterious effect of the cyclodiene at the higher cyclodiene:Pt ratios.

The total moles of cyclodiene provided to the process include the cyclodiene-platinum complex plus any additional non-complexed cyclodiene present in the process. Thus, where the process employs a cyclodiene-platinum complex as the catalyst, the additional non-complexed cyclodiene may be added to the process separate from the cyclodiene-platinum complex or may be provided to the process as a mixture with the cyclodiene-platinum complex. When the catalyst is a cyclodiene-platinum complex, it is desirable that the non-complexed cyclodiene be the same as that already complexed with the platinum although this is not a strict requirement.

The silyl hydride and/or hydrosiloxane employed in the reactions is not particularly limited. It can be, for example, any compound chosen from hydrosilanes or hydrosiloxanes including those compounds of the formulas $R^9_m SiH_p X_{4-(m+p)}$ or $M_a M^H_b D_c D^H_d T_e T^H_f Q_g$, where each $R^9$ is independently a substituted or unsubstituted aliphatic or aromatic hydrocarbyl group, X is halide, alkoxy, acyloxy, or silazane, m is 1-3, p is 1-3, and M, D, T, and Q have their usual meaning in siloxane nomenclature, with the proviso that when X is halide, the unsaturated substrate is not an alkyne. The subscripts a, b, c, d, e, f, and g are such that the molar mass of the siloxane-type reactant is between 100 and 100,000 Dalton. In one embodiment, an "M" group represents a monofunctional group of formula $R^{10}_3 SiO_{1/2}$, a "D" group represents a difunctional group of formula $R^{11}_2 SiO_{2/2}$, a "T" group represents a trifunctional group of formula $R^{12}SiO_{3/2}$, and a "Q" group represents a tetrafunctional group of formula $SiO_{4/2}$, an "$M^H$" group represents $HR^{13}_2 SiO_{1/2}$, a "$T^H$" represents $HSiO_{3/2}$, and a "$D^H$" group represents $R^{14}HSiO_{2/2}$. Each occurrence of $R^{10-14}$ is independently C1-C18 alkyl, C1-C18 substituted alkyl, C6-C14 aryl or substituted aryl, wherein $R^{10-14}$ optionally contains at least one heteroatom.

The instant invention also provides hydrosilylation with hydridosiloxanes comprising carbosiloxane linkages (for example, Si—$CH_2$—Si—O—SiH, Si—$CH_2$—$CH_2$—Si—O—SiH or Si-arylene-Si—O—SiH). Carbosiloxanes contain both the —Si-(hydrocarbylene)-Si— and —Si—O—Si— functionalities, where hydrocarbylene represents a substituted or unsubstituted, divalent alkylene, cycloalkylene or arylene group. The synthesis of carbosiloxanes is disclosed in U.S. Pat. No. 7,259,220; U.S. Pat. No. 7,326,761 and U.S. Pat. No. 7,507,775 all of which are incorporated herein in their entirety by reference. An exemplary formula for hydridosiloxanes with carbosiloxane linkages is $R^{15}R^{16}R^{17}Si(CH_2R^{18})_x SiOSiR^{19}R^{20}(OSiR^{21}R^{22})_y OSiR^{23}R^{24}H$, wherein R15-$R^{24}$ is independently a monovalent alkyl, cycloalkyl or aryl group such as methyl, ethyl, cyclohexyl or phenyl. Additionally, $R^{15-24}$ independently may also be H. The subscript x has a value of 1-8, y has a value from zero to 10 and, in embodiments, is zero to 4. A specific example of a hydridocarbosiloxane is $(CH_3)_3 SiCH_2CH_2Si(CH_3)_2OSi(CH_3)_2H$.

As used herein, "unsaturated" refers to a compound comprising one or more double or triple bonds. In one embodiment, unsaturated refers to a compound comprising carbon-carbon double or triple bonds. The unsaturated compound containing at least one unsaturated functional group employed in the hydrosilylation reaction is generally not limited and can be chosen from an unsaturated compound as desired for a particular purpose or intended application. The unsaturated compound can be a mono-unsaturated compound or it can comprise two or more unsaturated functional groups. In one embodiment, the unsaturated group can be an aliphatically unsaturated functional group. Examples of suitable compounds containing an unsaturated group include, but are not limited to, unsaturated polyethers such as alkyl-capped allyl polyethers, vinyl functionalized alkyl capped allyl or methylallyl polyethers; terminally unsaturated amines; alkynes (except with hydrochlorosilanes); C2-C45 linear or branched olefins, in one embodiment alpha olefins; terminally unsaturated dienes; unsaturated epoxides such as allyl glycidyl ether and vinyl cyclohexene-oxide; terminally unsaturated acrylates or methacrylates; unsaturated aryl ethers; aliphatically unsaturated aromatic hydrocarbons; unsaturated cycloalkanes such as trivinyl cyclohexane; vinyl-functionalized polymer or oligomer; vinyl-functionalized and/or terminally unsaturated allyl-functionalized silane and/or vinyl-functionalized silicones; unsaturated fatty acids; unsaturated fatty esters; or combinations of two or more thereof. Illustrative examples of such unsaturated substrates include, but are not limited to, ethylene, propylene, isobutylene, 1-hexene, 1-octene, 1-octadecene, styrene, alpha-methylstyrene, cyclopentene, norbornene, 1,5-hexadiene, norbornadiene, vinylcyclohexene, allyl alcohol, allyl-terminated polyethyleneglycol, allylacrylate, allyl methacrylate, allyl glycidyl ether, allyl-terminated isocyanate- or acrylate prepolymers, polybutadiene, allylamine, methallyl amine, methyl undecenoate, acetylene, phenylacetylene, vinyl-pendent or vinyl-terminal polysiloxanes, vinylcyclosiloxanes, vinylsiloxane resins, other terminally-unsaturated alkenyl silanes or siloxanes, vinyl-functional synthetic or natural minerals, etc.

Unsaturated polyethers suitable for the hydrosilylation reaction include polyoxyalkylenes having the general formula:

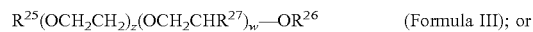  (Formula III); or

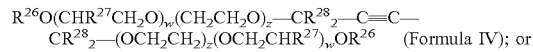  (Formula IV); or

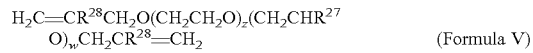  (Formula V)

wherein $R^{25}$ denotes an unsaturated organic group containing from 2 to 10 carbon atoms such as vinyl, allyl, methallyl, propargyl or 3-pentynyl. When the unsaturation is olefinic, it is desirably terminal to facilitate smooth hydrosilylation. However, when the unsaturation is a triple bond, it may be internal. $R^{26}$ is independently hydrogen, an alkyl group, e.g., from 1 to 8 carbon atoms such as the alkyl groups $CH_3$, n-$C_4H_9$, t-$C_4H_9$ or i-$C_8H_{17}$, and an acyl group, e.g., $CH_3COO$, t-$C_4H_9COO$, the beta-ketoester group such as $CH_3C(O)CH_2C(O)O$, or a trialkylsilyl group. $R^{27}$ and $R^{28}$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^{28}$ may also be hydrogen. In embodiments, $R^{27}$ and $R^{28}$ are methyl groups. Each occurrence of z is 0 to 100 inclusive and each occurrence of w is 0 to 100 inclusive. In embodiments, z and w are 1 to 50 inclusive.

In accordance with aspects of the present technology, when the unsaturated compound is a terminal alkyne, the silylhydride is a silylhydride other than a halosilane.

The present process can also be used, for example, for preparing a silylated polyurethane. This may include the step of contacting a terminally-unsaturated polyurethane with a silylhydride in the present of a platinum catalyst and the cyclodiene additive.

The hydrosilylation process is conducted in the presence of a platinum catalyst. The platinum catalyst employed in the process is not particularly limited and can be chosen from a variety of platinum compounds including, but not limited to, platinum halides, platinum siloxane complexes such as Ashby's or Karstedt's catalyst, cycloalkadiene-platinum complexes, or various other common platinum compounds or complexes known in the art.

In one embodiment, the platinum catalyst comprises a platinum halide, a reaction product of a platinum halide and organosilicon compound having terminal aliphatic unsaturation, or combinations of two or more thereof. Suitable platinum halides include, but are not limited to, platinum dichloride, platinum dibromide, platinum tetrachloride, chloroplatinic acid (i.e. $H_2PtCl_6.6H_2O$), dipotassium tetrachloroplatinate (i.e. $K_2PtCl_4$), etc. A particularly suitable platinum halide is chloroplatinic acid. Platinum catalysts useful in the present invention also include the reaction product of a platinum halide with an organosilicon compound having terminal aliphatic unsaturation. Such catalysts are described, for example, in Willing, U.S. Pat. No. 3,419,593, which is incorporated by reference for its teaching of platinum catalysts useful in the present process. The platinum catalyst can be, for example, the reaction product of a solution of chloroplatinic acid in ethanol or 2-propanol optionally in combination with an ethereal solvent at various ratios, or the reaction products of platinum dichloride or chloroplatinic acid with 1,3-divinyl-1,1,3,3-tetramethyldisiloxane.

In one embodiment, the platinum catalyst comprises a cycloalkadiene-platinum complex described by formula or $Pt(R^{30})X_2$, where $R^{30}$ is a cycloalkadiene comprising about six to 20 carbon atoms and each X can be an independently selected halogen atom. In one embodiment, the cycloalkadiene comprises about 6 to 10 carbon atoms. Suitable cycloalkadienes for the cycloalkadiene-platinum complexes include, but are not limited to, cyclohexadiene, cycloheptadiene, cyclooctadiene, cyclodecadiene, and norbornadiene. 1,5-cyclooctadiene is a particularly suitable cycloalkadiene for the cycloalkadiene-platinum complexes. In one embodiment, the platinum catalyst is described by formula $Pt(R^{30})Cl_2$, where $R^{30}$ is 1,5-cyclooctadiene.

The concentration of platinum catalyst used in the present process can be varied. In one embodiment, the concentration of platinum is from about 100 parts per billion (ppb) to about 100 ppm; from about 500 ppb to about 70 ppm; from about 1 ppm to about 50 ppm; even from about 10 ppm to about 30 ppm. Here as elsewhere in the specification and claims, numerical values can be combined to form new and alternative ranges.

The platinum catalyst may be dissolved in solvent to improve ease of handling. The solvent is not limited and can be either polar or non-polar. Any solvent can be used in the method of the invention, as long as it facilitates the dissolution of the platinum catalyst, without deleterious effects.

The temperature range for the process of the hydrosilylation is from −50° C. to 250° C., preferably from 0° C. to 150° C. A variety of reactors can be used in the process of this invention. The process can be run as a batch reaction or a continuous reaction at ambient, sub-ambient, or supra-ambient pressures. In one embodiment, the reaction is carried out under an inert atmosphere. Selection is determined by factors such as the volatility of the reagents and products. Continuously stirred batch reactors are conveniently used when the reagents are liquid at ambient and reaction temperature. These reactors can also be operated with a continuous input of reagents and continuous withdrawal of dehydrogenatively silylated or hydrosilylated reaction product. With gaseous or volatile olefins and silanes, fluidized-bed reactors, fixed-bed reactors and autoclave reactors can be more appropriate.

The reaction may be conducted in the presence of a solvent. The solvent is not particularly limited. In embodiments, the solvent is chosen from a hydrocarbon, a halogenated hydrocarbon, an ether, an alcohol, or a combination of two or more thereof Accordingly, in some embodiments, the present invention is also directed to the compositions produced from the above described methods. These compositions contain the hydrosilylated products of the silylhydride and the compound having at least one unsaturated group. The hydrosilylated products that are produced by the process of the present invention have uses in the synthesis of silicone materials such as organosilanes for coupling agents, adhesives, products for agricultural and personal care applications, and silicone surfactant for stabilizing polyurethane foams.

The following examples are intended to illustrate, but in no way limit the scope of the present invention. All parts and percentages are by weight and all temperatures are in Celsius unless explicitly stated otherwise. All patents, other publications, and U.S. patent applications referred to in the instant application are incorporated herein by reference in their entireties.

EXAMPLES

Reactions and manipulations were performed under nitrogen, using standard Schlenk-line techniques. The chloroplatinic acid was employed as an alcoholic solution of hexachloroplatinic acid. COD was used either directly or as an alcoholic or toluene solution. The allylpolyether and $MD^HM$ were obtained internally. All other starting materials were purchased from a commercial source and used as received without further purification. Olefin:SiH molar ratio used for the reactions was between 1.1:1 and 1:1.

Example 1

Hydrosilylation of Allyl Methacrylate (AMA) with $SiMeCl_2H$ Using Diene Additives A 4-neck round bottomed flask was fitted with an addition funnel, a syringe port, an alcohol thermometer, a magnetic stir bar, and a straight water-condenser fitted on top with a dry ice condenser. The addition funnel was equipped with a N$_2$ inlet and the N$_2$ line was split with a t-piece attached to a bubbler before the reaction. The system was flushed with N$_2$ and was charged with the appropriate inhibitors. The SiMeCl$_2$H (16.5 g, 0.140 mol) was charged to the addition funnel. The round bottomed flask was charged with allyl methacrylate (19.7 g, 0.16 mol), chloroplatinic acid (2 ppm Pt), and cyclooctadiene (COD) solution in ethanol (0.39 μmol, equimolar to Pt), where COD was used as an additive. The reaction mixture was heated to 80° C. Approximately 1 mL of the chlorosilane was added and the reaction was monitored for an exotherm. Once an exothermic reaction was detected, the chlorosilane was slowly added as to maintain a reaction temperature between 80° C. and 90° C. After chlorosilane addition was complete, the reaction was heated to 80° C. for 90 min. After 90 min the heat was removed and the product at ambient temperature was decanted into a brown bottle and stored under a N$_2$ blanket. The material was analyzed by GC and NMR spectroscopy.

Comparative Example 1

Figure 2:
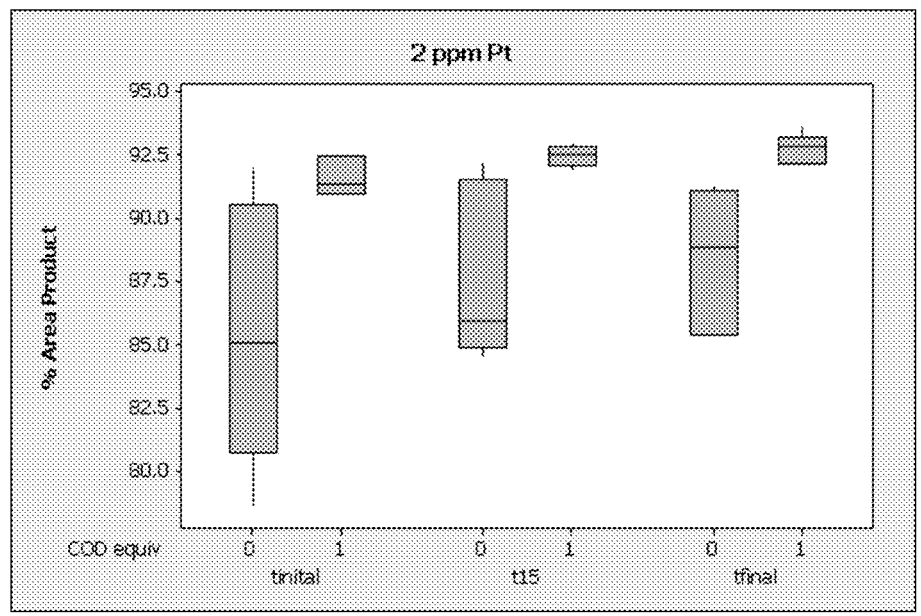
FIG. 2 is a graph showing the product yield for reactions of allyl methacrylate and SiMeCl$_2$H over time for reactions run with and without COD additives.

Hydrosilylation of Allyl Methacrylate with SiMeCl$_2$H without the Use of Diene Additives A reaction was run similarly to Example 1 except that COD solution was not added to the reaction. FIG. 1 shows the product yield evaluated by GC analysis for reactions of allyl methacrylate and SiMeCl$_2$H run with and without COD additives at 2 ppm of platinum. FIG. 2 shows the product the product yield over time with and without COD additives. The product yield was determined by GC analysis for reactions of allyl methacrylate and SiMeCl$_2$H run with and without COD additives at 2 ppm Pt. Aliquots were taken and analyzed by GC immediately after chlorosilane addition was complete (t initial), 15 minutes after chlorosilane addition was complete (t 15), and 90 minutes after chlorosilane addition was complete (t final).

Example 2

Hydrosilylation of Allyl Methacrylate with SiMeCl$_2$H Using Diene Additives Run to Evaluate the Color of the Reaction Product The reactions were run at a 5 ppm Pt loading similar to those discussed above, except the inhibitors which impart color were not added to the reaction. The color of the product was evaluated for reactions of allyl methacrylate and SiMeCl$_2$H run with various amount of COD equivalents.

TABLE 1

| COD equiv | Color (Pt/Co) |
| --- | --- |
| 0 | 331 |
| 0 | 193 |
| 0.5 | 150 |
| 1 | 46 |

Example 3

Hydrosilylation of Allyl Methacrylate with Si(OEt)$_3$H Using Diene Additives

A 4-neck round bottomed flask equipped with a magnetic stir bar, straight condenser, topped with a dry-ice condenser, syringe port, a liquid addition funnel, and a thermometer and placed under N$_2$. The reaction vessel was charged with inhibitors and allyl methacrylate (15 mL, 0.11 mol), the chloroplatinic acid solution (2 ppm Pt) COD solution (equimolar to Pt). The addition funnel was charged with the triethoxysilane (19 mL, 0.1 mol). The reaction was heated to 90° C. and then an aliquot of the triethoxysilane (3-5% by volume) was added and the reaction was monitored for exotherm. After exotherm was confirmed the remainder of the triethoxysilane was added via addition funnel at a rate to keep the reaction between 85° C. and 95° C. After final addition of the triethoxysilane, the reaction was heated for 90 minutes at 90° C. The resulting product was analyzed by GC and $^1$H NMR. The average Hazen value of the product for 4 separate runs was 111 Pt/Co.

Comparative Example 2

Figure 3:
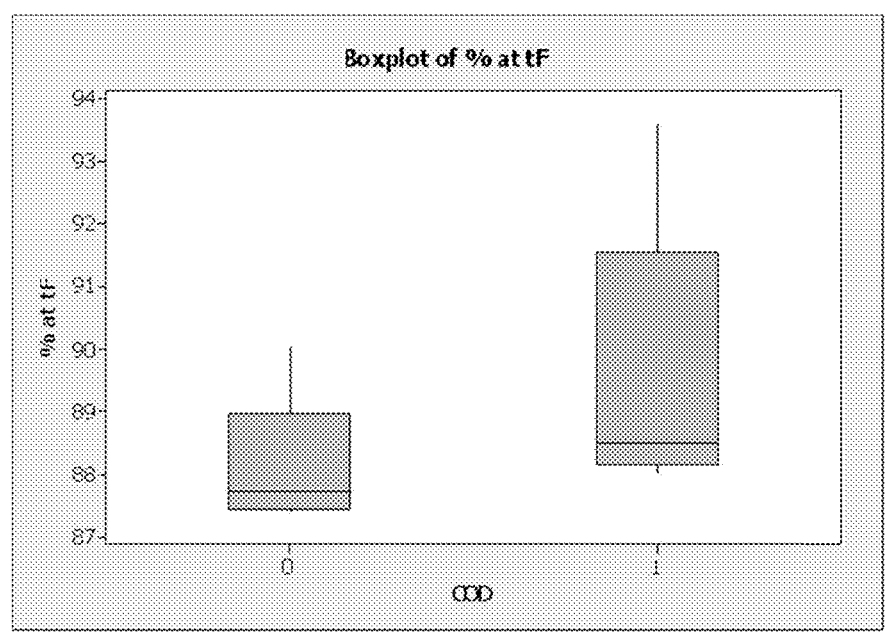
FIG. 3 is a graph showing the product yield for reactions of allyl methacrylate and Si(OEt)$_3$H as determined by GC analysis for reactions runs with and without COD additives.

Hydrosilylation of Allyl Methacrylate with Si(OEt)$_3$H without the Use of Diene Additives A reaction was run similarly as in Example 3 except that COD solution was not added to the reaction. The average Hazen value of the product for 4 separate runs was 171 Pt/Co. FIG. 3 compares the product yield as determined by GC analysis for Example 3 and Comparative Example 2 at 2 ppm of platinum.

Example 4

Hydrosilylation of Allylpolyether with MD$^H$M Using Diene Additives

A 4-neck round bottomed flask was equipped with a magnetic stir bar, an addition funnel, a syringe port, an alcohol thermometer, and a straight water-condenser fitted with a t-piece to accommodate N$_2$ flow. The system was flushed with N$_2$ and was charged with the MD$^H$M (5 mL, 0.02 mol) and methoxypolyethyleneglycolallylether (39.4 g, 0.1 mol). The remaining MD$^H$M (15 mL, 0.06 mol) was charged to the addition funnel. The round bottomed flask was charged with the COD solution (1.76 μmol, equimolar to Pt). The reaction mixture was heated to 80° C. The chloroplatinic acid solution (6 ppm Pt) was added to the mixture. The MD$^H$M was slowly added as to maintain a reaction temperature below 120° C. After addition of the MD$^H$M was complete, the reaction was heated to 80° C. for 60 min. The material was analyzed by NMR spectroscopy. The average Hazen value of the product for 3 separate runs was 32 Pt/Co.

Comparative Example 3

Hydrosilylation of Allylpolyether with MD$^H$M without the Use of Diene Additives A reaction was run similarly to Example 4 except that COD solution was not added to the reaction. The average Hazen value of the product for 3 separate runs was 78 Pt/Co.

Example 5

Hydrosilylation of Allyl Glycidyl Ether (AGE) with Si(OEt)$_3$H Using Diene Additives A 4-neck round bottomed flask was equipped with a magnetic stir bar, a condenser, a septum, a liquid addition funnel, and a thermocouple and subsequently rendered inert with $N_2$. The reaction vessel was charged with AGE (44.6 g, 0.39 mol) and the liquid addition funnel was charged with triethoxysilane (53.4 g, 0.33 mol). Subsequently, 5% of the triethoxysilane volume was added to the reaction vessel and the mixture heated to 90° C. Glacial acetic acid (44 μL) and the appropriate amount of COD solution were injected via syringe, followed by the injection of the chloroplatinic acid catalyst solution (250 ppb Pt). After confirmation of a reaction exotherm, the remainder of the triethoxysilane was added via addition funnel at a rate aimed at keeping the reaction temperature between 85° C. and 95° C. After final addition of the triethoxysilane, the temperature was maintained at 90° C. for an additional 2 hours. The resulting product mixture was analyzed by GC for % product area.

Comparative Example 4

Figure 4:
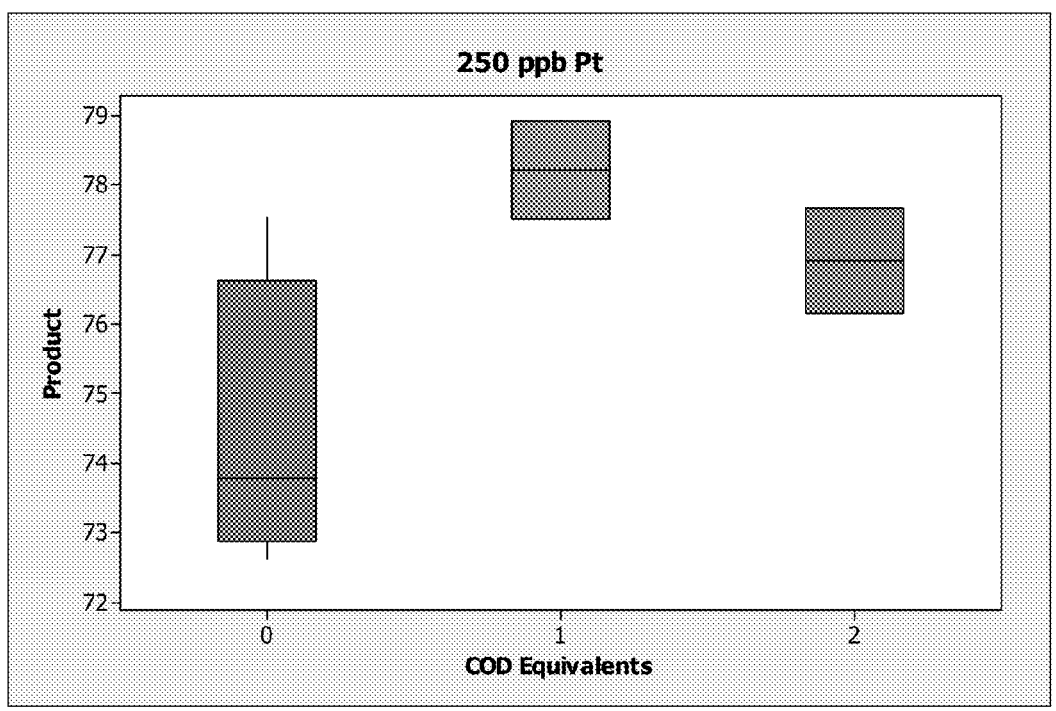
FIG. 4 is a graph showing the analyses of product mixtures for reactions of allyl glycidyl ether and Si(OEt)$_3$H run without COD and with 2 different ratios of COD to Pt.

Hydrosilylation of Allyl Glycidyl Ether with $Si(OEt)_3H$ without the Use of Diene Additives A reaction was run similarly as in Example 5 except that COD solution was not added to the reaction. FIG. 4 shows the product yield for Example 5 (at 1 and 2 equivalents of COD) and Comparative Example 4.

Example 6

Hydrosilylation of Allyl Methacrylate with $SiCl_3H$ Using Diene Additives

A 3-neck round bottomed flask was fitted with a syringe pump feeding across a septum, thermocouple connected to a temperature controller controlling a heating mantle, a magnetic stir bar, and a straight water-condenser fitted on top equipped with a $N_2$ inlet to a mineral oil bubbler. The system was flushed with $N_2$ and the round bottom flask was charged was charged with the allyl methacrylate (11.37 g, 0.09 mol) and appropriate inhibitors. The $SiCl_3H$ was charged to the syringe pump. The syringe pump was set on a feed rate of 0.14 mL/min and total feed volume was set to 8.41 mL (11.27 g, 0.08 mol). The reaction mixture was heated to 80° C. At 80° C. the reaction mixture was charged with chloroplatinic acid solution (3.3 ppm Pt), and COD solution in ethanol (0.38 μmol, equimolar to Pt), where COD was used as an additive. The chlorosilane feed was started and added over 1 hour. The exotherm was seen and reached a maximum temperature of 94.7° C. after 7 minutes onto the addition. After chlorosilane addition was complete the reaction mixture was cooled to ambient temperature and analyzed by GC. The composition of the reaction mixture was 75.3% product.

Comparative Example 5

Hydrosilylation of Allyl Methacrylate with $SiCl_3H$ without the Use of Diene Additives A 3-neck round bottomed flask was fitted with a syringe pump feeding across a septa, thermocouple connected to a temperature controller controlling a heating mantle, a magnetic stir bar, and a straight water-condenser fitted on top equipped with a $N_2$ inlet to a mineral oil bubbler. The system was flushed with $N_2$ and the round bottomed flask was charged was charged with the allyl methacrylate (11.37 g, 0.09 mol) and appropriate inhibitors. The $SiCl_3H$ was charged to the syringe pump. The syringe pump was set on a feed rate of 0.14 mL/min and total feed volume was set to 8.41 mL (11.27 g, 0.08 mol). The reaction mixture was heated to 80° C. At 80° C. the reaction mixture was charged with chloroplatinic acid solution (6.5 ppm Pt). The chlorosilane feed was started and added over 1 hour. The exotherm was seen and reached a maximum temperature of 90.2° C. after 5 minutes onto the addition. After chlorosilane addition was complete the reaction mixture was cooled to ambient temperature and analyzed by GC. The composition of the reaction mixture was 73.2% product.

Examples 7-8

Hydrosilylation of an OH-Terminated Methallylpolyether with a Carbosiloxyhydride Examples 7 and 8 and Comparative Examples 6-7 illustrate the effective use of 1,5-cyclooctadiene (COD) in the platinum-catalyzed, solventless hydrosilylation of uncapped methallyl polyethers by the carbodisiloxane, $(CH_3)_3SiCH_2CH_2Si(CH_3)_2OSi(CH_3)_2H$. The reaction products are intermediates in the synthesis of materials useful for making contact lens (See U.S. Patent Publications 2012/0244088 and 2012/0245249)

The carbodisiloxane was synthesized as disclosed in U.S. Pat. No. 7,259,220. The polyethers were the four and ten ethoxylates of methallyl alcohol. The four ethoxylate has a molecular weight of 248.32. The ten ethoxylate has a molecular weight of 512.64. Each polyether was reacted with and without addition of COD. Karstedt's catalyst was the platinum source in each experiment.

TABLE 2

QUANTITIES OF RAW MATERIALS USED IN Examples 7 and 8 and Comparative Examples 6 and 7

|  | Comparative Example 6 | Example 7 | Comparative Example 7 | Example 8 |
|---|---|---|---|---|
| Carbodisiloxane | 110.51 g<br>0.47 mole | 110.51 g<br>0.47 mole | 110.51 g<br>0.47 mole | 110.51 g<br>0.47 mole |
| Four ethoxylate of methallyl alcohol | 116.00 g<br>0.47 mole | 116.00 g<br>0.47 mole |  |  |
| Ten ethoxylate of methallyl alcohol |  |  | 240.00 g<br>0.47 mole | 240.00 g<br>0.47 mole |
| Karstedt's Catalyst | 25 ppm Pt | 25 ppm Pt | 25 ppm Pt | 25 ppm Pt |

TABLE 2-continued

QUANTITIES OF RAW MATERIALS USED IN Examples 7 and 8 and Comparative Examples 6 and 7

| | Comparative Example 6 | Example 7 | Comparative Example 7 | Example 8 |
|---|---|---|---|---|
| COD | None | 7 μL (6.2 mg) | None | 7 μL (6.2 mg) |
| SiH Test | Positive after 19 h reaction time | Negative after 19 h reaction time | Positive after 19 h reaction time | Negative after 19 h reaction time |

Each reaction was conducted in a 500 mL, 4-neck round bottomed flask fitted with a temperature-controlled heating mantle, mechanical stirrer, reflux condenser and Claisen connection. A serum cap was placed over the fourth neck. A thermocouple and nitrogen inlet line were affixed to the Claisen connection.

Equimolar quantities of carbodisiloxane and polyether were used because of the absence of isomerization with methallyl groups. In each experiment, the carbodisiloxane and polyether were added to the reaction flask and stirred vigorously while the environment in the flask is made inert with a slow flow of nitrogen. A small sample was withdrawn by syringe and analyzed by FTIR to establish the initial absorbance of the SiH vibration at 910 $cm^{-1}$. The temperature was then increased to 80° C. and the platinum catalyst was injected by syringe through the serum cap. An exotherm was observed and the temperature was maintained at 100° C. overnight (19 hours total reaction time). In Examples 7 and 8, 7 microliters COD (approx. 1:1 ratio of COD:Pt) were also added by syringe at 80° C. just prior to the catalyst injection.

Both the KOH test and analysis by FTIR were done to determine whether SiH functional groups were still present in the reaction mixture at intervals and after overnight heating. At the end, hydrogen was generated when the KOH test was applied to the reaction mixtures of Comparative Examples 6 and 7. The FTIR spectrum of each sample also showed pronounced absorbance at 910 $cm^{-1}$ indicating that unreacted SiH was present. In contrast, the reaction mixtures of Examples 7 and 8 tested negatively for SiH in both analyses.

The reaction products were stripped of volatiles in vacuo and later characterized by $^{13}C$, $^{1}H$ and $^{29}Si$ NMR. $^{29}Si$ NMR showed that conversion of SiH functionality in Comparative Example 7 was not only due to the desired reaction with the methallyl group (Si—C bond formation), but also to reaction with the terminal hydroxyl group (Si—O—C bond formation) of the polyether. Si—O—C bond formation was ~20 percent in the control (Comparative Example 7) and negligible in Example 8. Thus, use of COD as an additive was effective in completing the hydrosilylation of methallyl polyethers and suppressing the formation of SiOC by-products.

Example 9

Hydrosilylation of 1-Octene with Si(OEt)₃H Using Diene Additives

All glassware was dried in an oven at 125° C., overnight, prior to use. A 4-neck round bottom flask was fitted with an addition funnel, two rubber septa, a magnetic stir bar, and a water condenser fitted with a dry ice condenser. The addition funnel was equipped with a N₂ inlet and the N₂ line was split with a t-piece attached to a bubbler whose exit was passed through a scrubber filled with a KOH/ethanol solution (to quench any SiH₄ formed). A J-Kem temperature probe connected to a heating mantle was introduced through one rubber septum. The set-up was purged with N₂ flow, and the 4-neck round bottom was charged with 1-octene (37.2 g, 0.32 mol), 1,5-cyclooctadiene in toluene (0.14 mg, 1.28 μmol) as a 1.1 molar equivalent vs Pt. The mixture was blanketed with N₂. An amount of triethoxysilane (48.7 g, 0.29 mol was added to the addition funnel and purged with N₂. An additional amount of triethoxysilane (2.56 g, 0.016 mol) was added to the reaction mixture in the round bottom. The mixture in the round bottom was heated to 75° C. At 75° C. the reaction mixture was charged with acetic acid (0.18 g, 0.2 wt %), after which a chloroplatinic acid solution (2.5 ppm Pt, 1.14 μmol) was added, and the reaction was monitored for an exotherm. Upon confirmation of the exotherm (>5° C. temperature increase), the reaction was closely monitored and kept below 85° C. with the aid of a cool air gun. The triethoxysilane was added at a rate to keep the temperature between 80° C. and 85° C., with assistance as needed from a heating mantle or cool air gun. After final addition of triethoxysilane the resulting solution was allowed to stir at 80° C. for 60 minutes. At the end of 60 minutes the reaction was sampled for GC analysis, removed from heat, and was cooled to room temperature. The composition of the crude mixture by GC was 92.1% product. The Hazen value for the crude product was 22 Pt/Co.

Comparative Example 8

Hydrosilylation of 1-Octene with Si(OEt)₃H without the Use of Diene Additives

The reaction was run similarly to Example 9 except that COD solution was not added to the reaction. The composition of the crude mixture by GC was 92.8% product with a Hazen Value of 33 Pt/Co.

Example 11

Hydrosilylation of 1-Octene with Si(OEt)₃H Using Diene Additives

All glassware was dried in an oven at 125° C., overnight, prior to use. A 4-neck round bottom flask was fitted with an addition funnel, two rubber septa, a magnetic stir bar, and a water condenser fitted with a dry ice condenser. The addition funnel was equipped with a N₂ inlet and the N₂ line was split with a t-piece, attached to a bubbler whose exit was passed through a scrubber filled with a KOH/ethanol solution (to quench any SiH₄ formed). A J-Kem temperature probe connected to a heating mantle was introduced through one rubber septum. The set-up was purged with N₂ flow, and the reaction vessel was charged with 1-octene (82.24 g, 0.72 mol), 1,5-cyclooctadiene (0.54 mg, 4.98 μmol, 2 molar equivalents vs Pt), and the mixture was blanketed with $N_2$. An amount of triethoxysilane (105.9 g, 0.63 mol), was added to the addition funnel and purged with $N_2$. An additional amount of triethoxysilane (5.34 g, 0.032 mol) was added to the reaction via a syringe pump. The mixture in the round bottom was heated to 70° C. At 70° C. the reaction mixture was charged with aniline (0.136 g, 0.07 wt %). The reaction temperature was increased to 72.5° C. at which Karstedt's solution (2.5 ppm Pt, 2.49 μmol), was added and the reaction was monitored for an exotherm. Upon confirmation of the exotherm, the triethoxysilane was added at 2 mL/min and the reaction temperature was held at 72.5° C.+/−1.5° C. After final addition of triethoxysilane the resulting solution was allowed to stir at 70° C. for 60 minutes. At the end of 60 minutes the reaction was sampled for GC analysis, removed from heat, and was cooled to room temperature. The composition of the crude mixture by GC was 94.1% product. The Hazen value for the crude product was 30 Pt/Co.

Comparative Example 9

Hydrosilylation of 1-Octene with Si(OEt)₃H without the Use of Diene Additives

The reaction was run similarly to Example 11 except that COD solution was not added to the reaction. The composition of the crude mixture by GC was 93.7% product with a Hazen Value of 43 Pt/Co.

While the above description contains many specifics, these specifics should not be construed as limitations on the scope of the invention, but merely as exemplifications of preferred embodiments thereof. Those skilled in the art may envision other possible variations that are within the scope and spirit of the invention as defined by the claims appended hereto.

What is claimed is:
1. A process for the hydrosilylation of an unsaturated compound comprising reacting (a) a silyl hydride with (b) an unsaturated compound in the presence of (c) a platinum compound and (d) a cyclodiene, with the provisos that (i) when the unsaturated compound is a terminal alkyne, the silyl hydride is other than a halosilane, and (ii) when the platinum compound is a Pt(II)-based compound, the ratio of total moles of cyclodiene to moles of platinum is less than 3:1.

2. The process of claim 1, wherein the cyclodiene is chosen from a compound of the formula:

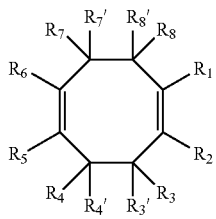

wherein $R^1$-$R^8$, $R^{3'}$, $R^{4'}$, $R^{7'}$, and $R^{8'}$ are independently hydrogen; an substituted or unsubstituted alkyl or aryl group optionally containing at least one heteroatom; an alkoxy; and a halogen radical; optionally $R^1$-$R^2$ and/or $R^5$-$R^6$ taken together may form a ring structure.

3. The process of claim 1, wherein the cyclodiene comprises 1,5-cyclooctadiene; 1,5-dimethyl-1,5-cyclooctadiene; 1,6-dimethyl-1,5-cyclooctadiene, or a combination of two or more thereof.

4. The process of claim 1, wherein the platinum compound is a Pt(II)-based compound, and the ratio of total moles of cyclodiene additive to moles of platinum is less than 2:1.

5. The process of claim 1, wherein the platinum compound is a Pt(II)-based compound, and the ratio of total moles of cyclodiene additive to moles of platinum is about 1:1 or lower.

6. The process of claim 1, wherein the platinum compound is a Pt(II)-based compound, and the ratio of total moles of cyclodiene additive to moles of platinum is from about 0.1:1 to about 2:1.

7. The process of claim 1, wherein the unsaturated compound is chosen from an unsaturated polyether; an alkyl capped allyl polyether; a methylallyl polyether; a terminally unsaturated amine; an alkyne; a C2-C45 linear or branched olefin; an unsaturated epoxide; a terminally unsaturated acrylate; a terminally unsaturated methacrylate; a terminally unsaturated diene; an aliphatically unsaturated aryl ether; an aliphatically unsaturated aromatic hydrocarbon; an unsaturated cycloalkane; a vinyl-functionalized polymer or oligomer; a vinyl-functionalized and/or terminally unsaturated allyl-functionalized or alkenyl-functionalized silane or siloxane; an unsaturated fatty acid; an unsaturated fatty ester; an aliphatically unsaturated synthetic or natural mineral; or a combination of two or more thereof.

8. The process of claim 1, wherein the unsaturated compound is chosen from polyoxyalkylenes having the general formula:

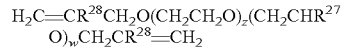

wherein $R^{25}$ is independently an unsaturated organic group containing from 2 to 10 carbon atoms; $R^{26}$ is independently hydrogen, an acyl group, or an alkyl group having from 1 to 8 carbon atoms; $R^{27}$ is independently a monovalent hydrocarbon group; $R^{28}$ independently chosen from hydrogen and a monovalent hydrocarbon group; each occurrence of z is 0 to 100 inclusive; and each occurrence of w is 0 to 100 inclusive.

9. The process of claim 1, wherein the silylhydride is chosen from a compound of the formula $R^9_m SiH_p X_{4-(m+p)}$ and/or $M_a M^H_b D_c D^H_d T_e T^H_f Q_g$, where each $R^9$ is independently a substituted or unsubstituted aliphatic or aromatic hydrocarbyl group, X is alkoxy, acyloxy, halogen, or silazane, m is 1-3, p is 1-3 the subscripts a, b, c, d, e, f, and g are such that the molar mass of the silylhydride is between 100 and 100,000 Dalton; M represents a monofunctional group of formula $R^{10}_3 SiO_{1/2}$, a D represents a difunctional group of formula $R^{11}_2 SiO_{2/2}$, a T represents a trifunctional group of formula $R^{12} SiO_{3/2}$, Q represents a tetrafunctional group of formula $SiO_{4/2}$, $M^H$ represents $HR^{13}_2 SiO_{1/2}$, $T^H$ represents $HSiO_{3/2}$, and $D^H$ represents $R^{14} HSiO_{2/2}$; each occurrence of $R^{10-14}$ is independently C1-C18 alkyl, C1-C18 substituted alkyl, C6-C14 aryl or substituted aryl, wherein R10-14 optionally contains at least one heteroatom.

10. The process according to claim 1, wherein the silylhydride is a chlorosilane.

11. The process of claim 1, wherein the silylhydride is a compound of the formula $R^{15}R^{16}R^{17}Si(CH_2R^{18})_xSiOSiR^{19}R^{20}(OSiR^{21}R^{22})_yOSiR^{23}R^{24}H$, where $R^{15}$-$R^{24}$ are independently chosen from hydrogen, a monovalent alkyl group, a cycloalkyl group, and an aryl group; x has a value of 1-8, and y has a value from zero to 10.

12. The process of claim 11, wherein the ratio of cyclodiene to platinum is about 1:1.

13. The process of claim 1, wherein the platinum compound is chosen from platinum halides, platinum siloxane complexes, cycloalkadiene-platinum complexes, or a combination of two or more thereof.

14. The process of claim 1, wherein the platinum compound is chloroplatinic acid.

15. The process of claim 1, wherein the platinum compound is a Pt(0)-based compound.

16. The process of claim 15, wherein the platinum compound is chosen from a vinylsiloxane-complexed Pt catalyst.

17. The process of claim 15 where the ratio of cyclodiene to Pt(0) is 0.1:1 to 100:1.

18. The process according to claim 1 where the unsaturated compound is allyl methacrylate.

19. The process of claim 1, wherein the unsaturated compound is allyl glycidyl ether.

20. The process of claim 1 where the unsaturated compound is an allyl or methallyl polyether.

21. The process of claim 1 where the reaction is carried out at a temperature of −50° C. to 250° C.

22. The process of claim 1 where the reaction is conducted in the presence of a solvent chosen from a hydrocarbon, a halogenated hydrocarbon, an ether, an alcohol, or a combination of two or more thereof.

23. The process of claim 1, wherein the platinum concentration is from about 100 parts per billion to about 100 parts per million.

* * * * *